US010130699B2

(12) United States Patent
Jacobs et al.

(10) Patent No.: US 10,130,699 B2
(45) Date of Patent: *Nov. 20, 2018

(54) VACCINE AGAINST LAWSONIA INTRACELLULARIS AND PORCINE CIRCOVIRUS 2

(71) Applicant: Intervet Inc., Madison, NJ (US)

(72) Inventors: Antonius Arnoldus Christiaan Jacobs, Kessel (NL); Vicky Fachinger, Bad Soden (DE); Melanie Sno, Venlo (NL); Maarten Hendrik Witvliet, Oostrum (NL)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/100,880

(22) PCT Filed: Dec. 2, 2014

(86) PCT No.: PCT/EP2014/076223
§ 371 (c)(1),
(2) Date: Jun. 1, 2016

(87) PCT Pub. No.: WO2015/082457
PCT Pub. Date: Jun. 11, 2015

(65) Prior Publication Data
US 2016/0303218 A1 Oct. 20, 2016

(30) Foreign Application Priority Data

Dec. 3, 2013 (EP) .................................... 13195515
Oct. 1, 2014 (EP) .................................... 14187317

(51) Int. Cl.
*A61K 39/12* (2006.01)
*A61K 39/02* (2006.01)
*C12N 7/00* (2006.01)
*A61K 39/00* (2006.01)

(52) U.S. Cl.
CPC .......... *A61K 39/12* (2013.01); *A61K 39/0241* (2013.01); *A61K 39/105* (2013.01); *C12N 7/00* (2013.01); *A61K 2039/521* (2013.01); *A61K 2039/54* (2013.01); *A61K 2039/552* (2013.01); *A61K 2039/55511* (2013.01); *A61K 2039/55566* (2013.01); *A61K 2039/575* (2013.01); *A61K 2039/70* (2013.01); *C12N 2750/10034* (2013.01); *C12N 2750/10071* (2013.01)

(58) Field of Classification Search
None
See application file for complete search history.

(56) References Cited

FOREIGN PATENT DOCUMENTS

| WO | 1997020050 A1 | 6/1997 | |
|----|---------------|--------|---|
| WO | 2005011731 A1 | 2/2005 | |
| WO | WO2005009462 A2 | 2/2005 | |
| WO | 2007028823 A1 | 3/2007 | |
| WO | 2007094893 A2 | 8/2007 | |
| WO | 2008076915 A2 | 6/2008 | |
| WO | 2009144088 A2 | 3/2009 | |
| WO | WO2009127684 A1 | 10/2009 | |
| WO | WO 2010106095 A1 * | 9/2010 | ........... A61K 9/0019 |
| WO | WO201315208 A2 | 10/2013 | |
| WO | 2006099561 A1 | 9/2017 | |

OTHER PUBLICATIONS

Porcilis PCV—Ideal Adjuvant (http://pcv2-mhyo.azurewebsites.net/Products/PorcilisPCV/Why/IdealAdjuvant, accessed Nov. 8, 2017).*
EMEA, Note for guidance: requirements for combined veterinary products, EMEA, 2000, p. 2/6, CVPMP/IVVP/52/97-FINAL.
International Search report for PCTEP2014076223—Feb. 26, 2015 dated Feb. 26, 2015, 4 pages.
Kis, Elsa et al, devices for intradermal vaccination, Vaccine, 2012, 523-538, 30, Elsevier.
N.N., Compatability of components, US Department of Health dan Human Services, 1997, p. 3, nN.N.
N.N., Vaccine safety Basics, Module 2, 2013, p. 53, N.N.
Kroll et al., Proliferative enteropathy: a global enteric disease of pigs caused by Lawsonia intracellularis, Animal Health Research Reviews, 2005, 173-197, 2005 6(02.
Eblé et al, Intradermal Vaccination of Pigs Against fmd with 1/10 Dose Results in Comparable Vaccine Afficacy as Intramuscular Vaccination With a Full Dose, Vaccine, 2009, pp. 1272-1278, vol. 27, Elsevier, JP.
Eizaburo DeGuchi, Changes in PCV 2 pig body dynamics by vaccination of porcine circovirus type 2 (PCV 2) and farm control, Swine 2011, pp. 32-35, vol. 39, Japan SPF porcine Association, JP abstract only.
L Ferrari et al, Evaluation of the immune response induced by intradermal vaccination by using a needle-less system in comparison with the intramuscular route in conventional pigs, Research in Veterinary Science, 2011, pp. 64-71, vol. 90, Elsevier, JP.
L Ferrari et al, Lymphocyte activation as cytokine gene expression and secretion is related to the porcine reproductive and respiratory syndrome virus, Veterinary Immunology and Immunopathology, 2013, pp. 193-206, vol. 151, JP.

* cited by examiner

*Primary Examiner* — Brian Gangle

(57) ABSTRACT

The present invention pertains to a vaccine comprising in combination killed whole cell Lawsonia intracellularis bacteria and porcine circo virus 2 (PCV2) ORF2 protein for use in protecting a pig against an infection with Lawsonia intracellularis and PCV2 by an intradermal administration of the vaccine. The invention also pertains to a method to protect a swine against an infection with Lawsonia intracellularis bacteria and PCV2.

16 Claims, 6 Drawing Sheets

2A

2B

2C

VACCINE AGAINST LAWSONIA INTRACELLULARIS AND PORCINE CIRCOVIRUS 2

CROSS-REFERENCE TO RELATED APPLICATIONS

This application is a national stage entry under 35 U.S.C. § 371 of PCT/EP2014/076223 filed on Dec. 2, 2014, which claims priority to EP Application No. EP14187317.4 filed on Oct. 1, 2014, and EP13195515.5 filed on Dec. 3, 2013. The content of PCT/EP2014/076223 is hereby incorporated by reference in its entirety.

GENERAL FIELD OF THE INVENTION

The invention in general pertains to the field of swine health. Swine are prone to many pathogenic micro-organisms. Control of infection is commonly done by stable and feed management, treatment with pharmaceuticals such as anti-viral drugs and antibiotics, or prophylactic treatment using vaccines.

OBJECT OF THE INVENTION

There is a continuous need for convenient, safe and efficacious means for the management of swine health.

SUMMARY OF THE INVENTION

In order to meet the object of the invention a new vaccine for the combined protection of swine against infections with various disease causing micro-organisms is devised, the vaccine comprising in combination killed whole cell Lawsonia intracellularis bacteria and porcine circo virus 2 (PCV2) ORF2 protein. PCV2 and Lawsonia intracellularis bacteria are both responsible for substantial economic losses due to their negative influence on swine health. Although drugs as well as vaccines are known and commercially available to treat PCV2 and/or Lawsonia infections, there is a continuous need for novel ways to provide good protection in a safe and convenient way. Combination vaccines against PCV2 and Lawsonia infection have been described but are not commercially available. Indeed, not all combinations of antigens contemplated or suggested, in particular not in each and every way of administration, may lead to a safe and effective combination vaccine. In fact, there is always a level of uncertainty with regard to safety and efficacy of the combination vaccine, in particular when the administration regime is altered.

The committee for veterinary medicinal products of the European Agency for the Evaluation of Medicinal Products (EMEA) in its publication "Note for guidance: requirements for combined veterinary products" (EMEA, 2000, CVMP/IWP/52/97-FINAL), stated (page 2/6) that the "development of combined vaccines is not straightforward. Each combination should be developed and studied individually in terms of quality, safety and efficacy". The committee further indicates that the search for a good combination vaccine typically includes the compatibility between the individual components in the combined vaccine, including for example preservatives, excipients and stabilisers, inactivating agents and adjuvants. On page 3, top paragraph, it is stated that "In combined vaccines, the presence of more than one component can often cause an interaction, leading to either a diminished or an increased response to individual components, compared to when the specific component(s) is administered alone . . . . Such interactions are often immunological in nature, but may also be caused by other factors with less direct effects on the immune system", and also "When an adjuvant is used to augment the immune response to a combined vaccine, special problems may appear."

The U.S. Department of Health and Human Services, Food and Drug Administration, Center for Biologics Evaluation and Research, published in April 1997 a "Guidance for Industry, for the evaluation of combination vaccines for preventable diseases: Production, Testing and Clinical Studies", in which guidance it is stated (page 3, under "Compatibility of Components") that "Experience has shown that combining monovalent vaccines may result in a new combination which is less safe or effective than desirable. Sometimes the components of inactivated vaccines may act adversely on one or more of the active components", indicating that especially an inactivated vaccine may negatively influence the efficacy of a live vaccine, such as for example occurred when combining a live pertussis vaccine and an inactivated poliovirus vaccine that resulted in a vaccine with decreased pertussis potency. It is indicated that any additional components in the vaccine might complicate the safety and potency of the final product when compared to the individual vaccines.

The World Health Organization (WHO) has published an e-learning course called "Vaccine Safety Basics", which in the MODULE 2 contemplates combination vaccines. This module starts with "Licensed combination vaccines undergo extensive testing before approval by national authorities to assure that the products are safe, effective, and of acceptable quality." It is also stated that "With all combinations, manufacturers must therefore evaluate the potency of each antigenic component, the effectiveness of the vaccine components when combined to induce immunity, risk of possible reversion to toxicity, and reaction with other vaccine components."

On page 53 of this e-learning course the WHO reports that "The route of administration is the path by which a vaccine (or drug) is brought into contact with the body. This is a critical factor for success of the immunization. A substance must be transported from the site of entry to the part of the body where its action is desired to take place. Using the body's transport mechanisms for this purpose, however, is not trivial."

The California Department of Health Services' Immunization Branch has published guidelines for correct immunization (http://www.cdc.gov/vaccines/pubs/pinkbook/downloads/appendices/d/vacc_admin.pdf). With regard to the administration site it is stated on page 7, first full paragraph that "The recommended route and site for each vaccine are based on clinical trials, practical experience and theoretical considerations. This information is included in the manufacturer's product information for each vaccine. There are five routes used in the administration of vaccines. Deviation from the recommended route may reduce vaccine efficacy or increase local adverse reactions." On page 14 the only US-licensed intradermal vaccine is addressed: "Fluzone Intradermal is the only U.S.-licensed vaccine that is administered by the intradermal route. It is approved only for use in persons 18 through 64 years of age. This Fluzone formulation is not the same as intramuscular formulations of inactivated influenza vaccine (TIV). Other TIV formulations should NOT be administered by the intradermal route."

All in all, any combination of particular antigens and a site of administration is not straightforward and requires experimentation to determine safety and efficacy.

The present invention, next to the vaccine as such, also pertains to a method to protect a swine against an infection with Lawsonia intracellularis bacteria and PCV2, comprising administering the said vaccine intradermally, and to a method to constitute such a vaccine.

Definitions

A vaccine is a constitution that protects against a (post vaccination) infection with a pathogenic micro-organism.

Protection against an infection with a pathogenic mirco-organism denotes preventing or reducing the infection by the micro-organism itself, or preventing or reducing a (sub-) clinical disease that results from the infection, typically by interfering with the micro-organism itself, for example via antibodies, in the vaccinated host.

A composition comprising killed whole cell bacteria as antigen comprises an antigenic constitution that is derived from the killing of live, whole cell, bacteria. This does not exclude that the bacterial cells are, at least partly, ruptured during the killing process, or that an extract or homogenate of the killed whole cells is actually provided as the antigen in the "vaccine comprising the killed whole cell bacteria" in the sense of the present invention. Killed whole cell Lawsonia intracellularis bacteria are for example known from WO2009/144088 and WO97/20050.

PCV2 ORF2 protein is the capsid protein of porcine circo virus type 2. The ORF 2 of PCV 2 encodes a protein of about 28 kDa. The ORF 2 of all PCV-2 isolates share 91-100% nucleotide sequence identity and 90-100% deduced amino acid sequence identity (Fenaux et al., J. Clin. Micorbiol., 38(7), 2494-2503, 2000). The ORF2 protein can for example be recombinantly expressed, for example in a baculo virus expression system, such as described in WO2007/028823, WO 2007/094893 or WO2008/076915.

Intradermal administration of a vaccine means a sufficient amount of the vaccine is deposited in dermis, leading to an immunological response significantly different (in particular: when using the Wilcoxon rank sum test in a test set up as outlined in Example 3, the p value should be less than 0.10, preferably less than 0.05) from an intramuscular administration with the same vaccine and volume thereof. Several devices are commercially available for intradermal vaccination, for example the IDAL® vaccinator (MSD Animal Health), the Pulse 50 MicroDose (Pulse Needle Free Systems), or other devices as described in *Vaccine*, 2012 Jan. 11; 30(3):523-38 (see in particular Table 1, page 525: "An overview of different devices for liquid and solid formulation administration")

Single shot administration of a vaccine for use in protecting means that in order to obtain protective immunity, the vaccination does not need to be boosted with a second administration. In a two-shot regime, the first (prime) vaccination is typically boosted within 6 weeks from the first administration, commonly within 3 or even 2 weeks from the first administration, and only after the second (boost) administration protective immunity is understood to be obtained.

A pharmaceutically acceptable carrier is a biocompatible medium, viz. a medium that after administration does not induce significant adverse reactions in the subject animal, capable of presenting the antigen to the immune system of the host animal after administration of the vaccine. Such a carrier can be a liquid containing water and/or any other biocompatible solvent, but can also be a solid such as commonly used to obtain freeze-dried vaccines (based on sugars and/or proteins).

EMBODIMENTS OF THE INVENTION

In an embodiment the vaccine is for protection of the pig after a single shot administration. It was advantageously found that a swine is protected against both pathogens even after a single shot administration of the vaccine. This embodiment does not exclude that a follow up vaccination is given, for example 6 to 12 months after the first vaccination to renew the level of protection. This follow up vaccination differs from a boost vaccination in a prime-boost vaccination scheme, wherein protection is only believed to be obtained after the boost vaccination. In a prime-boost scheme, the two vaccinations are typically 2-3 weeks apart.

In an embodiment the vaccine comprises an adjuvant. It was found that an adjuvant, which is typically used to improve the immune response of inactivated antigens, does not negatively interfere with the Lawsonia or PCV2 antigens when administering the vaccine into the dermis (which is a site known for its adverse reactions), nor excessively increases the reactivity to the other antigen, despite the WHO explicitly warns for this type of interference and reactivity in its Vaccine Safety Basics course (see above) on page 1 of the course, last two lines (section "Combination vaccines"). In a further embodiment the adjuvant comprises a non biodegradable oil, such as for example a saturated hydrocarbon oil which can be obtained from ExxonMobil® (Marcol® 52).

In an embodiment the vaccine further comprises inactivated *Mycoplasma* hyopneumoniae (Mhyo) antigens, preferably Mhyo bacterin. This has proven to lead to a convenient, safe and efficacious vaccine against three major swine pathogens.

In yet another embodiment the vaccine comprises per dose $1\times10^9$ killed Lawsonia intracellularis bacteria. i.e. the inactivated Lawsonia intracellularis antigens are at a load such that the vaccine comprises Lawsonia intracellularis antigen corresponding to $1\times10^9$ Lawsonia intracellularis bacteria per dose. A higher antigen load, which is not excluded in this embodiment, may positively influence the level of protection and duration of immunity.

In an embodiment the Lawsonia bacteria are freeze-dried prior to adding the bacteria to a composition, for example a PCV2 ORF2 comprising aqueous composition or emulsion, to constitute the vaccine.

The same way, in the method to constitute a vaccine for intradermal administration, the method comprising combining killed whole cell Lawsonia intracellularis bacteria and porcine circo virus 2 (PCV2) ORF2 protein with a pharmaceutically acceptable carrier, the killed whole cell Lawsonia intracellularis bacteria may be in freeze-dried form and added to a liquid formulation comprising the carrier and the PCV2 ORF2 protein, typically within 1 hour before administration.

The invention will be further explained using the following example and figures.

EXAMPLES

Example 1 is an experiment to show that a single dose intradermal vaccination can provide twenty three weeks of immunity against an infection with porcine circo virus type 2.

Example 2 is another experiment with a PCV2 ID once vaccination approach showing that vaccination is safe and leads to protective titers.

Example 3 is a direct comparison between intradermal and intramuscular vaccination.

Example 4 describes experiments with combined intradermal vaccination.

Example 5 describes an experiment with combination vaccines, various antigen dosages and various adjuvants.

Example 6 describes a further experiment with combination vaccines.

EXAMPLE 1

Experimental Design

Figure 1:
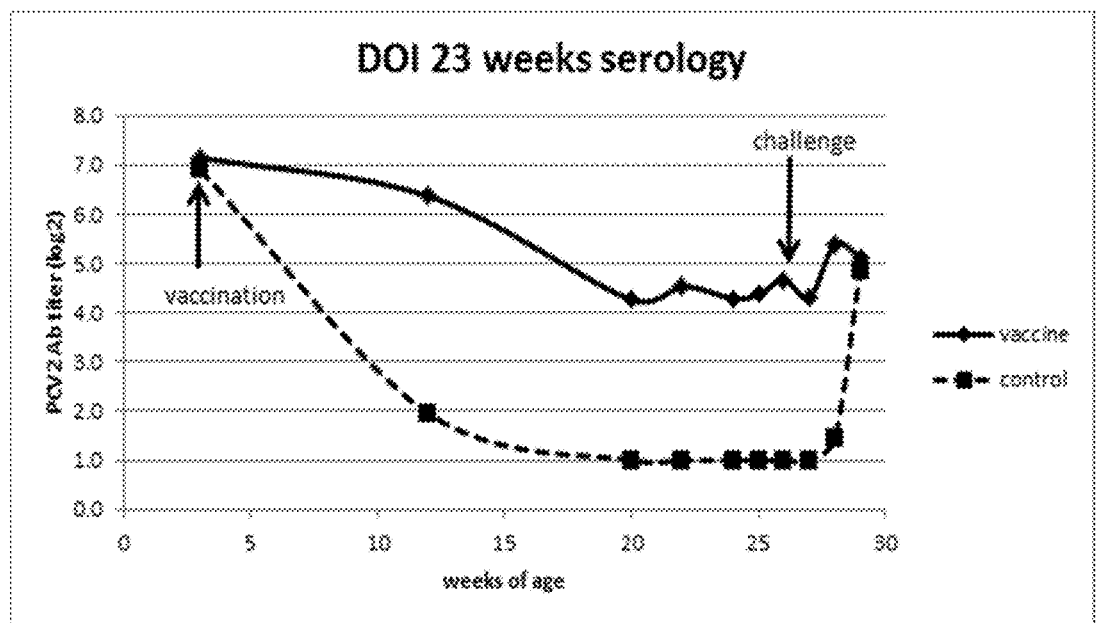
FIG. 1 Serology in a DOI study
FIG. 2A Viral load in serum.

Progeny of 10 sows with antibodies against PCV2 were used for this study. Piglets were divided across litters into 2 groups of 15 animal animals. At 3 weeks of age, the piglets of group 1 were vaccinated intradermally on the right side of the neck with 0.2 ml of a vaccine comprising recombinantly expressed ORF2 protein of porcine circo virus type 2 (see WO 2007/028823 for the provision of the protein), using the commercially available intradermal vaccination device IDAL® (available from MSD Animal Health, Boxmeer, The Netherlands), while group 2 was left unvaccinated and served as a control group. All study animals were observed daily for clinical signs. Blood samples of all animals were taken at time of vaccination, 9, 17, 19 and 21 weeks later. Twenty-three weeks following vaccination each animal was challenge infected using a wild-type PCV2 challenge virus strain applied intranasally.

Serum samples and fecal swabs were taken one day before challenge and one, two and three weeks after challenge and were examined for PCV2 viral nucleic acid by quantitative PCR. In addition serum samples were examined for PCV2 antibodies. Three weeks following challenge, all animals were necropsied and inguinal lymph node, tonsil and lung were sampled for determination of PCV2 viral antigen and nucleic acid.

The vaccine used was given as an oil-in-water emulsion, comprising 5% v/v of the mineral oil Marcol® 52 (Exxon), 0.30% w/v vitamin E acetate and 0.32% Polysorbate 80 (Tween 80; Sigma Aldrich), water for injection and 2000 AU of PCV2 protein per 0.2 ml. The AU units are calculated based on an AlphaLISA test of PerkinElmer. For this test the wells of a polystyrene microtitre-plate are filled with serial dilutions of test sample containing PCV2 ORF2 antigen alongside serial dilutions of a reference standard. These dilutions are incubated with acceptor-beads (coated with monoclonal antibody directed against PCV2 ORF2), and biotin-labeled secondary antibody which is also directed against PCV2 ORF2. The amount of bound secondary antibody is then quantified by incubation with streptavidin coated donor-beads and chemiluminescent detection. The reference standard is such that the commercially available vaccine Porcilis® PCV is set to contain 5000 AU per (2 ml) dose.

Experimental Procedure

Daily Observation

All pigs were observed daily for clinical signs of disease. Observations consisted of systemic reactions including loss of appetite, tendency to lie down, listlessness or drowsiness, shivering, bristling, oedema (especially around the eyes), vomiting, diarrhoea and dyspnoea.

Sampling of Blood

Blood samples were collected before vaccination, 9, 17, 19 and 21 weeks later. Blood samples were collected one day before challenge and 7, 13 and 19 days after challenge. This was done from all pigs individually.

Fecal Swabbing

Fecal swabs were taken from all animals, using one dry swab per animal, one day before challenge, 7, 13 and 18 days post challenge. Swabs were taken using standard procedures, into medium containing antibiotics. Suspensions of swabbed material in medium was clarified by centrifugation, aliquotted and stored at ≤−18° C. until further use.

Serology

All serum samples were examined for antibodies against PCV2, using standard ELISA procedures. In brief, serially diluted serum samples were incubated on microtiter plates coated with baculovirus expressed PCV2 ORF2 antigen. After removing the sera, all wells were incubated with a fixed amount of biotin-labeled PCV2-specific monoclonal antibody. Bound MoAb was then incubated with peroxidase-conjugated streptavidin followed by chromophoric detection. Titers were expressed as log 2 titers.

Postmortem Examination

At the end of the experiment all animals were euthanized by bleeding following stunning. During necropsy the animal was opened and the viscera are inspected in-situ, paying particular attention to the following organs: lungs, inguinal and mesenteric lymph nodes, tonsils, thymus, spleen, liver and kidneys. Following this, samples from tonsil, lung (lobus accessories), and inguinal lymph node were removed for quick freezing and later analysis by quantitative PCR (qPCR).

Quantitative PCR

Quantitative PCR (qPCR) was performed on all sera and fecal swabs, and on 10% tissue homogenates of tonsil, lung and inguinal lymph nodes. In brief, DNA was extracted from the samples using a commercial kit. PCV2 genomic DNA in each sample was quantified by polymerase chain reaction (PCR), using primers and a dually labeled hydrolysis probe specific for PCV2. The cycle number where specific fluorescence exceeded the threshold was correlated with the cycle numbers for a set of samples containing known amounts of a PCV2-containing plasmid. Results were expressed as log 10 copies/μl of reaction mixture (log 10 c/μl).

Results

At the start of the experiment all animals were found to be healthy. In the control group one animal was found dead at 6 weeks post vaccination (wpv). Two vaccinated animals had slight local problems, viz. a slight motional dysfunction (stiffness in one leg). Given the low problem, these animals were not treated. None of the vaccinated animals showed any signs of disease or systemic reactions such as hyperthermia, reduced feed intake, anaphylactic shock or vomiting.

The results of the serology are given in FIG. 1. It is clear that the vaccinated animals keep an anti-PCV2 titer that seems to level out to about 4.0 log 2, whereas in the control animals the titer decreases below the detection limit. After challenge (23 wpv, at an age of 26 weeks), titers slightly rise in the vaccinated group. In the control group titers rise to the same level.

Figure 2:
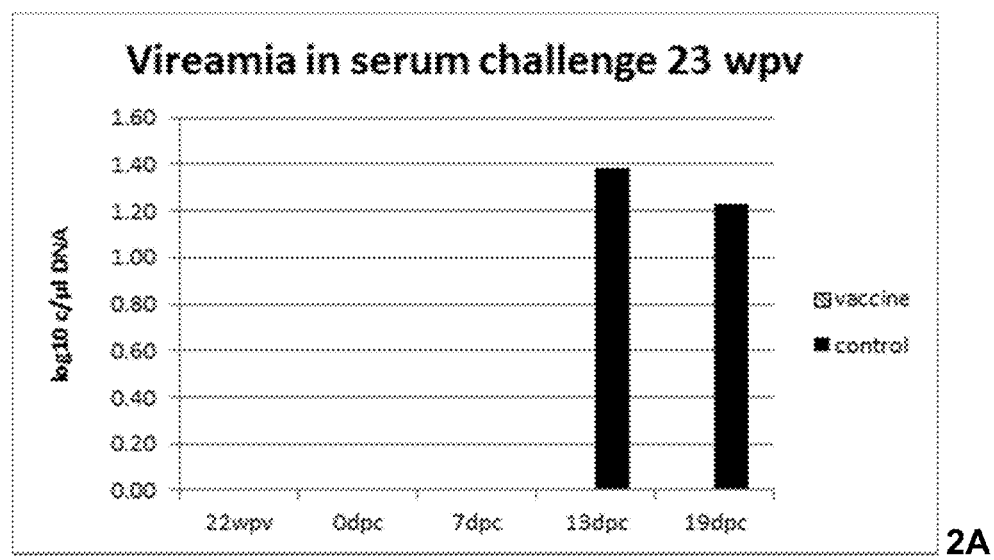
FIG. 2B Viral load in Feces
FIG. 2C Viral load in Organs
FIG. 3 Average body temperatures
FIG. 4 Average total PCV2 Ig Ab results
FIG. 5 Average PCV2 IgM Ab results
FIG. 6 Antibody titers in a duration study
FIG. 7 Viral load in organs
FIG. 8 Viral load in organs
Figure 2:
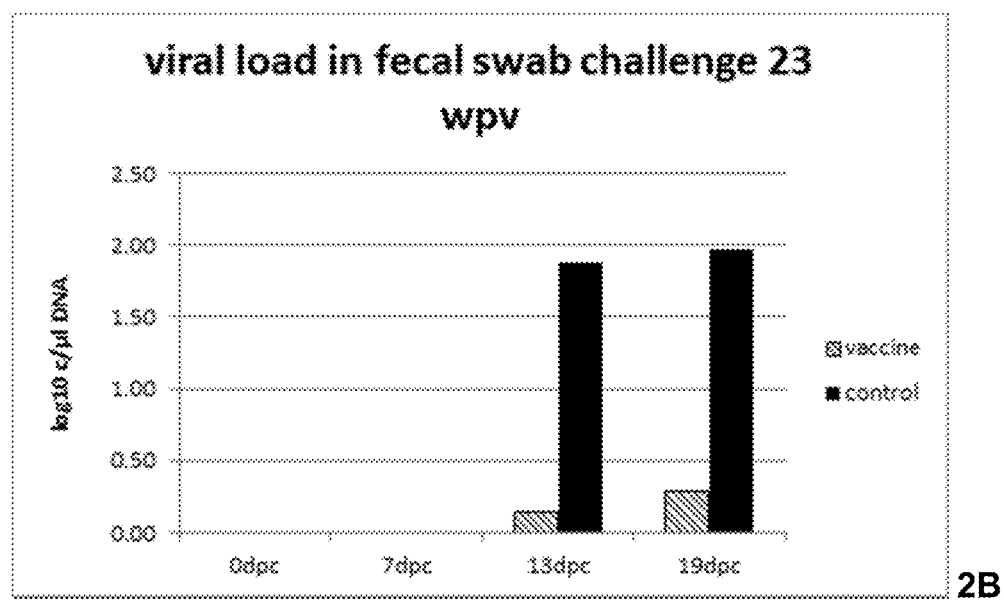
Figure 2:
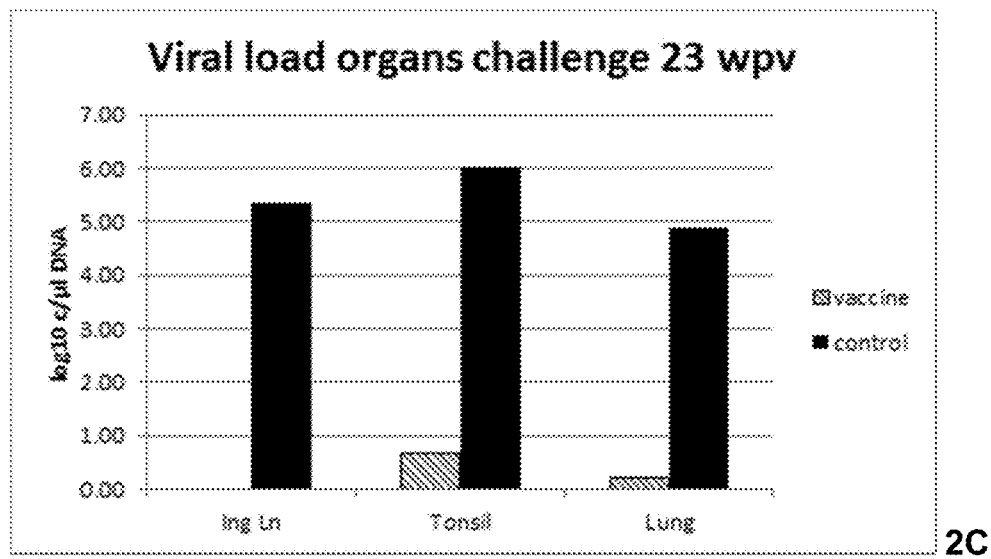

The qPCR results are shown in FIGS. 2A, 2B and 2C ("dpc"=days post challenge). It appears that the vaccinated animals, 23 weeks after vaccination were protected from challenge infection with PCV2, as shown by the significant reduction of PCV2 nucleic acid in serum, lymphoid organs and lung. Furthermore, the vaccine was capable to reduce the viral shedding as demonstrated by a significant reduction of the viral load in fecal swabs against PCV2 of at least 23 weeks. This was done in field animals, having circulating anti-body titers against PCV2 of approximately 7 log 2, which is considered a medium level.

EXAMPLE 2

Experimental Design

A total of 46 piglets from one farrowing batch were allotted to 4 treatment groups: two vaccinated groups of 13 piglets each and two control groups of 10 piglets. Group one was vaccinated as indicated above under Example 1 when the piglets were approximately two weeks old, group two was vaccinated when the piglets were approximately three weeks old. The piglets were intradermally vaccinated in the right side of the neck with a single dose of vaccine. Groups 3 (control group 2 week old animals) and 4 (control group 3 week old animals) were not vaccinated. Serum samples were collected from all animals on the day of vaccination, 2, 3 and 4 weeks after vaccination. Temperatures were taken one day before vaccination, at the day of vaccination and four hours later and at 1, 2, 3, 4 days post vaccination.

Experimental Procedure

Before vaccination, the piglets were observed for general health. Body temperatures were taken of all piglets, on day T=−1, day T=0 at 0 and 4 hours after vaccination, and on day T=1, 2, 3, 4 post vaccination.

Blood samples were collected on the day of vaccination and 2, 3 and 4 weeks later. This was done from all pigs individually according to standard procedures. The blood samples were collected without the addition of anti-coagulant. Serum was prepared from the clotted blood samples and aliquots were filled and stored at −20° C. until analysis.

Total PCV2 Ig antibody and PCV2 IgM antibody ELISA were tested as indicated here above under Example 1 ("Serology"), except that in the case of IgM antibody ELISA, the plates were coated with IgM antibody and thereafter incubated with PCV2 ORF2 antigen, before incubation with a fixed amount of biotin-labeled PCV2-specific monoclonal antibody.

Results

Figure 3:
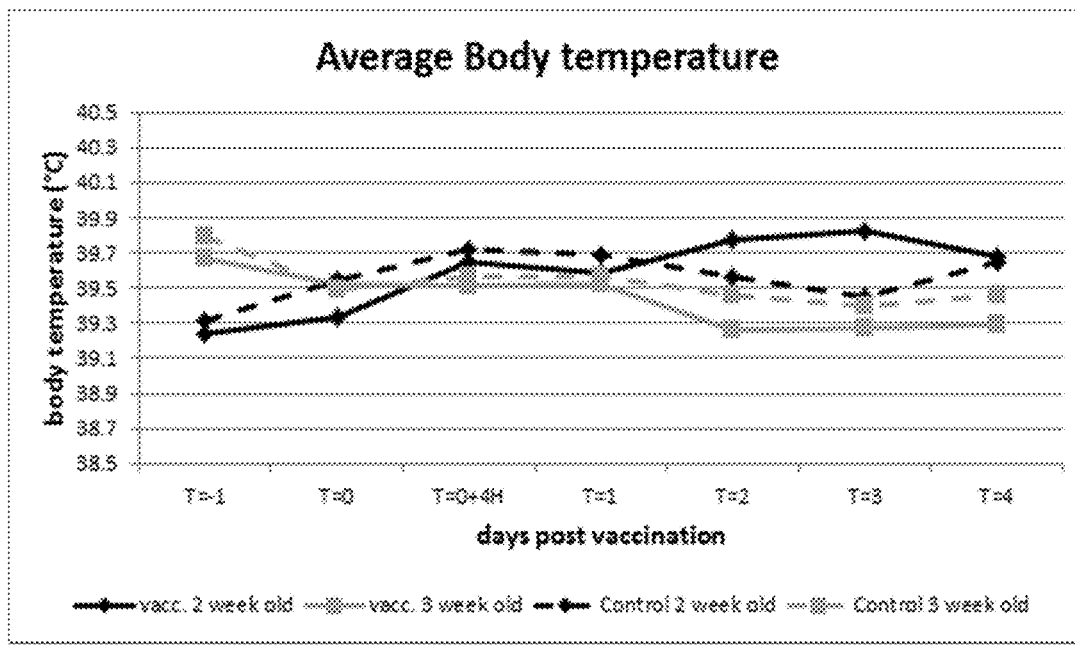

At the start of the experiment all animals were found to be healthy. Average results of the body temperatures are shown in FIG. 3. No difference could be seen in the average increase in body temperature between either the two and three week old animals (maximum average increase was between 0.0-0.3° C.). Also, the maximum increase in body temperature of individual animals in group 1 and in group 2 was comparable to the maximum temperature increase of individual animals in the two control groups.

Total PCV2 Ig Antibody ELISA

Figure 4:
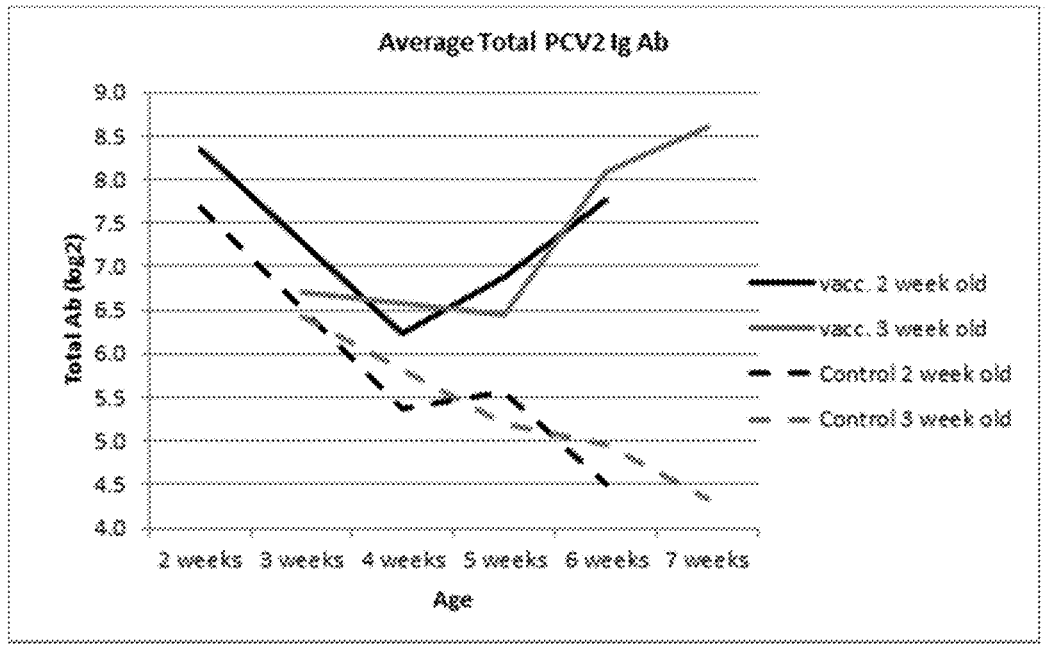

Average results of the total PCV2 Ig antibody response are summarized in FIG. 4.

At the time of vaccination, piglets vaccinated at 2 weeks of age had higher (most likely maternally derived) PCV2 antibody titers than piglets vaccinated at 3 weeks of age. The vaccinated animals showed an increase in titer considerably higher than the control animals.

PCV2 IgM Antibody ELISA

Figure 5:
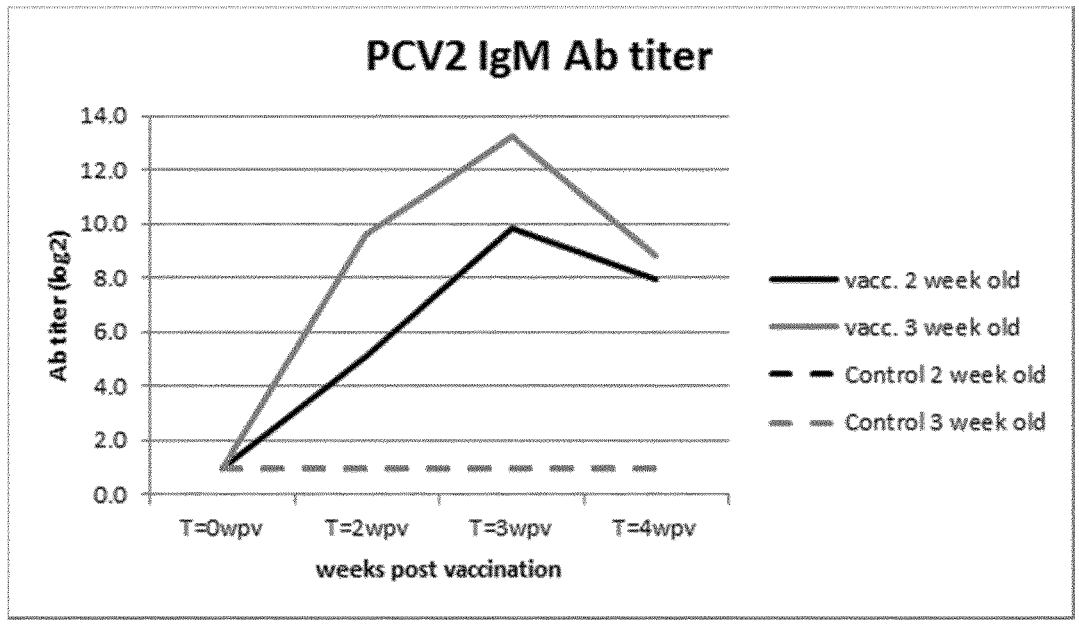

Average results of the PCV2 IgM antibody response are shown in FIG. 5. At the time of vaccination all animals were negative for IgM antibodies. Following vaccination the three week old animals had a considerable faster and higher IgM antibody response than the two week old animals. The control animals remained negative throughout the study.

Based on these results it may be concluded that the one dose intradermal vaccination of piglets at 2 and 3 weeks of age resulted in an acceptable safety profile and a good serological response. Comparable results were obtained with another experiment (data not shown) where the starting level of circulating anti-body titers was even higher, viz. up to 9.4 log 2, which is considered to be at the high end of a medium range.

EXAMPLE 3

Experimental Design

A total of 30 piglets were allotted to three treatment groups of 30 piglets each. Piglets from group 1 were intradermally vaccinated with a single dose of vaccine as indicated hereabove under Example 1. Piglets from group 2 were intramuscular vaccinated with a single dose of the same vaccine, in the same amount at the same place (in the neck), and piglets from group 3 were left untreated. Serum samples were collected from all animals on the day of vaccination, three and five weeks after vaccination.

Experimental Procedure

Before vaccination, the piglets were observed for general health, according to standard procedures. Sampling of blood and serology of total anti-PCV2 antibodies and PCV2 ORF2 specific IgM antibodies was done according to the procedure as indicated here above under Example 2.

Results

At the start of the study all animals were found to be healthy. Results of the serology are summarised in Table 1 (titers expressed as log 2). At the time of vaccination mean antibody titers were relatively high. Following vaccination, none of the animals showed an increase in PCV2 Ab titer. At 3 and 5 weeks post vaccination, in the ID group higher mean PCV2 antibody titers than in the IM group could be observed.

Results of the anti PCV2 IgM serology are summarised in Table 2 (titers expressed as log 2). At three weeks post vaccination anti PCV2 IgM antibody titers of the ID group was considerably higher than of the IM group and the control group.

TABLE 1

Average antibody results

| Groups | Titer 0 wpv | Titer 3 wpv | Titer 5 wpv |
|---|---|---|---|
| 1 | 8.2 | 7.3 | 6.2 |
| 2 | 8.6 | 6.5 | 5.1 |
| 3 | 8.4 | 6.2 | 4.3 |

TABLE 2

Average anti PCV2 IgM antibody results

| Group | IgM titer 3 wpv |
|---|---|
| 1 | 12.7 |
| 2 | 3.4 |
| 3 | 1.0 |

When applying the Wilcoxon rank sum test, the p value for the difference in IgM response for the ID group versus the IM group was 0.0001.

EXAMPLE 4

Progeny of several sows with antibodies against PCV2 were available for this study. Piglets were divided across litters into 3 groups of 18 animals. At 3 weeks of age, the piglets of group 1 and 2 were vaccinated intradermally as indicated here above under Example 1. The animals in group 2 were vaccinated intradermally at the same time with the commercially available inactivated Mhyo vaccine Porcilis® M Hyo ID Once (containing an Mhyo bacterin) according to manufacturer's instructions at the other side of the neck. Animals of group 3 (control group) remained untreated. All study animals were observed daily. Serum samples were taken at the time of vaccination and every other week until animals were sent to slaughter (23-25 weeks of age). These samples were examined for PCV2 antibodies.

Figure 6:
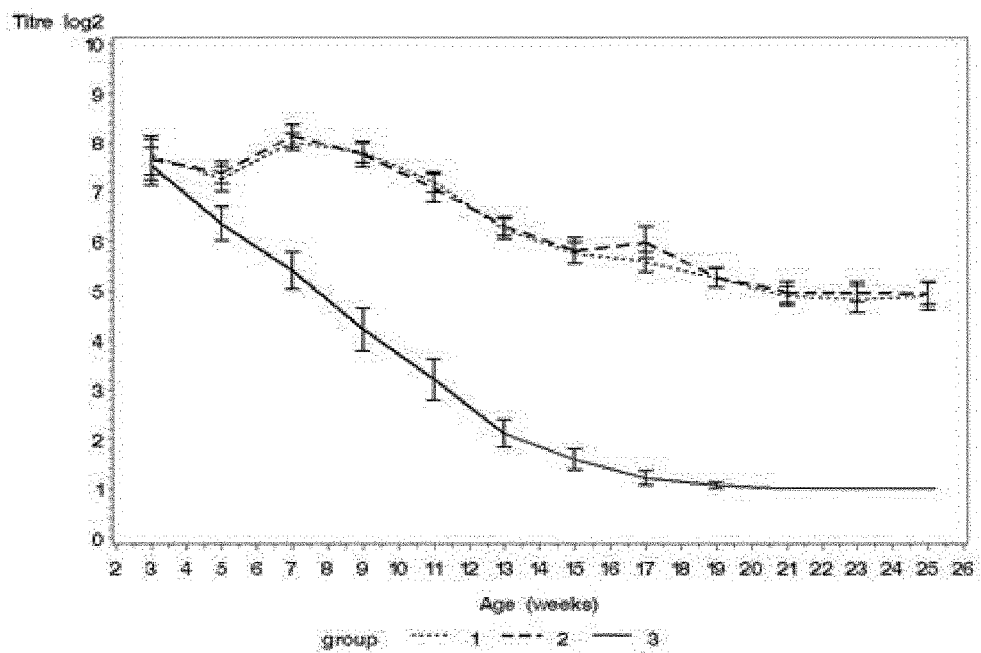

Experimental procedures were as indicated here above under Example 1. The resulting serology is shown in FIG. 6. From this figure it becomes clear that the anti-PCV2 titers remain well above the level of 4 log 2 as established with the experiments as described under Example 1 and found to be protective. There is no indication of negative interference between the vaccines.

This experiment was repeated to check protection against virulent *Mycoplasma hyopneumoniae*. For this repeat experiment sixty piglets were used. Forty animals were vaccinated at the age of 18-24 days with the Mhyo vaccine and twenty of these animals were also vaccinated with the PCV vaccine. Twenty animals were not vaccinated and served as challenge controls. Three weeks after vaccination all animals were infected with a virulent *M. hyopneumoniae* strain and three weeks post-challenge all animals were post-mortem investigated for lung lesions. Lung lesion scores (LLS) were compared between the groups.

The LLS for the groups vaccinated with Porcilis® M Hyo ID Once were significantly lower than those of the control group (p<0.05, Dunn's test). There was no significant difference between the groups that had been vaccinated with Porcilis® M Hyo ID Once alone or in association with the PCV vaccine. It may thus be concluded that the combined vaccination has no negative effect on the immunity obtained with Porcilis® M Hyo ID Once.

EXAMPLE 5

In total eight vaccines were formulated containing PCV2 ORF2 protein (250 to 6000 AU/0.2 ml), M hyo (at the same level as in Porcilis® Mhyo ID Once) and Lawsonia antigen (see WO 20089/127684, example 2 for the killed whole cells antigens: at a level of approximately $1\times10^9$ cells per 0.2 ml). The vaccines contained different adjuvants. Some vaccines used the existing biodegradable oil containing adjuvant Diluvac Forte (MSD Animal Health, Boxmeer, The Netherlands; called "DF"). Others used the adjuvant formulation as described here above under Example 1 (called "X-solve 12"), or adjuvants formulated with the same constituents as X-solve 12, but at half of the concentrations (called "X-solve 6"), or 2½ times the concentrations as in X-solve 12 (called "X-solve 30"). The resulting vaccines were as follows (the Mhyo and Lawsonia antigens are not recited; content per dose):

Group 1: 2000 AU PCV2/X-solve 30
Group 2: 250 AU PCV2/X-solve 12
Group 3: 500 AU PCV2/X-solve 12
Group 4: 2000 AU PCV2/X-solve 12
Group 5: 2000 AU PCV2/X-solve 6
Group 6: 500 AU PCV2/DF
Group 7: 2000 AU PCV2/DF
Group 8: 6000 AU PCV2/DF The progeny of 8 sows were used for this study. The piglets had moderate (medium level) maternally derived antibodies (MDA) against PCV2 (average: 6.7 log 2). At three/four weeks of age the piglets from groups one through eight were vaccinated intradermally with a single dose, using an IDAL® vaccinator. Piglets from group nine remained unvaccinated. At seven weeks post vaccination all animals were transported to the challenge facilities. One day later all animals were challenge infected with a challenge strain of PCV2. All piglets were observed daily for clinical signs.

Local reactions were monitored by palpation, starting on the day of vaccination and every two days after vaccination until twenty days post vaccination.

Blood samples were collected from all animals on the day of vaccination and three weeks later, one day before challenge, 1 and 2 weeks later and at the time of necropsy. Serum samples taken from each animal were tested for antibodies against PCV2 and M hyo. During necropsy, mesenteric and inguinal lymph node, tonsil and lung were sampled for quantification of PCV2 nucleic acid.

Experimental procedures were the same as described here above under Example 2. PCV2 IgM antibody response at time of vaccination was below detection level for all groups (below 2.0 log 2). At 3 weeks post vaccination the PVC antibody titer was the highest for the 2000AU PCV2/X-solve 30 vaccine, viz. 20 log 2. The X-solve 12 groups, comprising 250-, 500- and 2000 AU PCV2 antigen per dose had a titer of 9, 16 and 19 log 2 respectively. The group that received the 2000 AU/X-solve 6 vaccine had a titer of 15 log 2. The DF groups comprising the 500-, 2000- and 6000 AU of PCV2 antigen per dose had a titer of 8, 14 and 16 log 2 respectively. The controls had a titer below detection level.

In this study, systemic and local reactions were assessed. No systemic reactions attributable to vaccination were observed. As far as local effects are concerned, no more than three vaccinated animals (having received the X-solve 12 500 and 2000 AU, or DF 6000 AU PCV2 per dose vaccine respectively) had slight motility problems, the same number as in the control animals. Therefor these reactions may reasonably be regarded as unrelated to the vaccination. With regard to other local reactions, many animals (between about 60-100%) vaccinated with X-solve showed local reactions, the average size of the swellings was less than 3 cm, viz. between 1-2 cm, and the swellings disappeared within 2-6 days. Using DF, only about 30% of the animals showed local swellings, the mean size being less than 0.5 cm, and they disappeared within a day.

Figure 7:
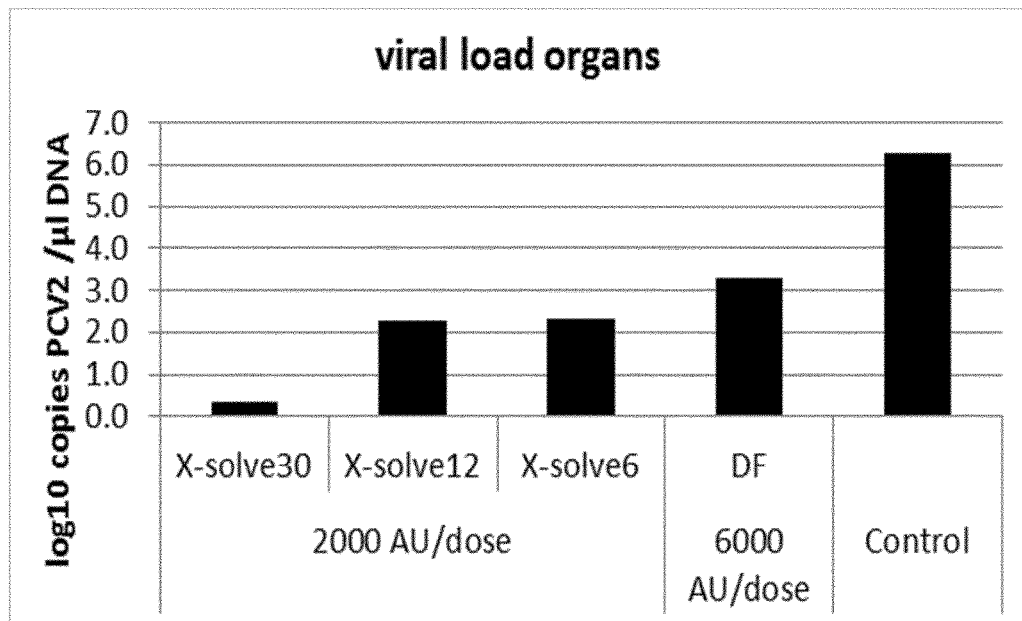
Figure 8:
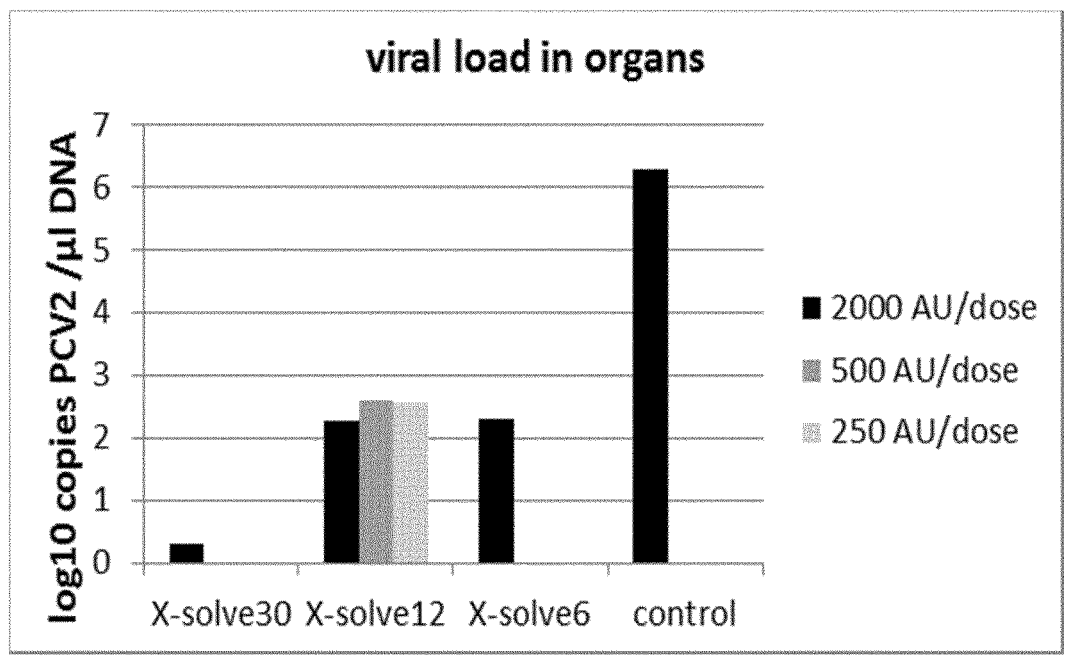

In FIGS. 7 and 8 the viral load in the organs (averaged) is depicted for the various vaccines. It appears that all vaccines are able to substantially (in these cases at least 3 logs) reduce the viral load in the relevant organs.

In this study it appeared that all adjuvants used were safe, induced an anti PCV2 IgM response and were able to treat an animal against an infection with pathogenic porcine circo virus type 2. No negative interference between the different antigens was found. Lawsonia serology (not shown) shows a good antibody response, based on which it is believed that protection against an infection with Lawsonia intracellularis was obtained. In order to confirm this, a next experiment including a challenge with pathogenic Lawsonia intracellularis was conducted (see Example 6).

EXAMPLE 6

In order to confirm that animals are protected against a challenge with Lawsonia intracellularis, vaccine formulation with different amounts of the adjuvant X-solve, as described in Example 5, were newly formulated for various challenge experiments. The basis for these vaccines was a PCV2 vaccine containing PCV2 ORF2 protein. A first vaccine was formulated in X-solve 30 as indicated in Example 5. A second vaccine was formulated in X-solve 12, wherein Lawsonia antigen was introduced by adding freeze-dried killed Lawsonia cells (the same antigen as used in Example 5) to the ready-to-use PCV2 vaccine within 30 minutes before administration. The end concentration of PCV2 ORF2 protein in both vaccines was 2000 AU/0.2 ml. The concentration of Lawsonia antigen was the same as used for the experiments as described in Example 5 (about $1 \times 10^9$ cells per 0.2 ml). The resulting vaccines were as follows:

1: 2000 AU PCV2/Lawsonia/X-solve 30
2: 2000 AU PCV2/Lawsonia/X-solve 12

A first study was performed using vaccine number 1 (X-solve 30). Thirty-nine pigs were used, allotted to two groups of 19 and 20 pigs respectively. Both groups were vaccinated at the age of three weeks with 0.2 ml of the vaccine by intradermal vaccination in the neck as indicated in Example 1. The first group was vaccinated with vaccine number 1 as indicated here above, the second group with the same vaccine but without the Lawsonia antigens. This group served as a control for the Lawsonia challenge. All animals were challenged at the age of 22 weeks. Unacceptable safety issues were not seen. The results regarding average daily weight gain (during days 14-21 post challenge), ileum scores (3 weeks after challenge; the score is proportional to the presence of ileum lesions due to the presence of a Lawsonia infection) and PPE incidence are indicated in Table 3. Statistically different values (two-sided tests, p<0.05; ANCOVA test for ADWG, cumulative logit model for the Ileum score and Fischer's exact test for PPE incidence) are indicated with an asterisk.

TABLE 3

| Vaccine | ADWG in kg | Ileum score | PPE incidence |
|---|---|---|---|
| Vaccine 1 | 1.100* | 50* | 4/19* |
| Control vaccine | 0.886 | 83.5 | 11/20 |

A second study was performed using vaccine number 2 (X-solve 12). Fifty pigs were used, allotted to two groups of 25 pigs each. One group was vaccinated at the age of three weeks with the vaccine indicated here above as number 2 with 0.2 ml of this vaccine by intradermal vaccination in the neck as indicated in Example 1. The second group was not vaccinated and served as a control. All animals were challenged at the age of 24 weeks. The results regarding average daily weight gain (during days 13-20 post challenge), ileum scores (3 weeks after challenge; the score is proportional to the presence of ileum lesions due to the presence of a Lawsonia infection) and PPE incidence are indicated in Table 4. Statistically different values (two-sided tests, p<0.05; ANCOVA test for ADWG, cumulative logit model for the Ileum score and Fischer's exact test for PPE incidence) are indicated with an asterisk. During the test in each group 1 animal had to be euthanized due to a-specific, non vaccine related problems.

TABLE 4

| Vaccine | ADWG in kg | Ileum score | PPE incidence |
|---|---|---|---|
| Vaccine 2 | 1.001* | 129* | 11/24* |
| None | −0.053 | 241 | 22/24 |

The results show that the intradermal vaccination of an animal with a combined vaccine comprising PCV2 ORF2 protein and killed Lawsonia intracellularis bacteria provide protection against an infection with pathogenic Lawsonia intracellularis. Also, the freeze-drying of Lawsonia antigen prior to formulation appears to have no negative effect on efficacy.

The invention claimed is:

1. A method to protect a swine against an infection with Lawsonia intracellularis bacteria and porcine circo virus 2 (PCV2), comprising administering into the dermis of the animal a vaccine comprising in combination killed whole cell Lawsonia intracellularis bacteria and PCV2 ORF2 protein; wherein said vaccine comprises less than 12.5% (v/v) mineral oil.

2. The method of claim 1, that leads to protection after a single shot administration of the vaccine.

3. The method of claim 2, wherein the vaccine further comprises inactivated Mycoplasma hyopneumoniae (Mhyo) antigens.

4. The method of claim 3, wherein the inactivated Mycoplasma hyopneumoniae antigens comprise a Mycoplasma hyopneumoniae bacterin.

5. The method of claim 4, wherein the amount of killed Lawsonia intracellularis bacteria in the vaccine per dose is $1 \times 10^9$.

6. The method of claim 5, wherein the Lawsonia bacteria are freeze-dried prior to adding the bacteria to a composition to constitute the vaccine.

7. The method of claim 1, wherein the amount of killed Lawsonia intracellularis bacteria in the vaccine per dose is $1 \times 10^9$.

8. The method of claim 7, wherein the vaccine further comprises inactivated Mycoplasma hyopneumoniae (Mhyo) antigens.

9. The method of claim 8, wherein the inactivated Mycoplasma hyopneumoniae antigens comprise a Mycoplasma hyopneumoniae bacterin.

10. The method of claim 9, wherein the Lawsonia bacteria are freeze-dried prior to adding the bacteria to a composition to constitute the vaccine.

11. A method to protect a swine against an infection with *Lawsonia intracellularis* bacteria and PCV2, comprising administering into the dermis of the animal a vaccine comprising in combination killed whole cell *Lawsonia intracellularis* bacteria and porcine circo virus 2 (PCV2) ORF2 protein; wherein said vaccine further comprises an adjuvant comprising an oil-in-water emulsion with less than 12.5% (v/v) mineral oil.

12. The method of claim 11, that leads to protection after a single shot administration of the vaccine.

13. The method of claim 11, wherein the amount of killed *Lawsonia intracellularis* bacteria in the vaccine per dose is $1 \times 10^9$.

14. The method of claim 11, wherein the vaccine further comprises inactivated *Mycoplasma hyopneumoniae* (Mhyo) antigens.

15. The method of claim 14, wherein the inactivated *Mycoplasma hyopneumoniae* antigens comprise a *Mycoplasma hyopneumoniae* bacterin.

16. The method of claim 15, wherein the Lawsonia bacteria are freeze-dried prior to adding the bacteria to a composition to constitute the vaccine.

\* \* \* \* \*